United States Patent [19]

Umezawa et al.

[11] 4,169,939

[45] Oct. 2, 1979

[54] PROCESSES FOR THE PRODUCTION OF 3',4'-DIDEOXYKANAMYCIN B

[75] Inventors: Hamao Umezawa; Sumio Umezawa, both of Tokyo; Tsutomu Tsuchiya, Yokohama, all of Japan

[73] Assignee: Zaidan Hojin Biseibutsu Kagaku Kenkyu Kai, Tokyo, Japan

[21] Appl. No.: 851,019

[22] Filed: Nov. 14, 1977

[30] Foreign Application Priority Data

Dec. 16, 1976 [JP] Japan ............................ 51-150334

[51] Int. Cl.$^2$ ............................................ C07H 15/22
[52] U.S. Cl. .................................. 536/10; 536/17 R; 424/180
[58] Field of Search ............................ 536/10, 17

[56] References Cited

U.S. PATENT DOCUMENTS

| Re. 28,647 | 12/1975 | Umezawa et al. | 536/10 |
|---|---|---|---|
| 3,868,360 | 2/1975 | Daniels et al. | 536/17 |
| 3,929,762 | 12/1975 | Umezawa et al. | 536/10 |

FOREIGN PATENT DOCUMENTS

| 1349302 | 4/1974 | United Kingdom | 536/10 |

OTHER PUBLICATIONS

Umezawa, S. et al., Bull. Chem. Soc. Japan, 45 (12), 3624-3628 (1972).
Jikihara, T. et al., Bull. Chem. Soc. Japan, 46 (11), 3507-3510 (1973).
Umezawa et al., Jour. of Antibiotics, XXIV (7), 485-487 (1971).
Umezawa et al., Jorn. of Antibiotics, XXV (12), 743-745 (1972).

*Primary Examiner*—Johnnie R. Brown
*Assistant Examiner*—Blondel Hazel
*Attorney, Agent, or Firm*—Herbert W. Taylor, Jr.

[57] ABSTRACT

A clinically valuable antibiotic, 3',4'-dideoxykanamycin B is now produced by a reduced number of consecutive steps in an improved overall yield by new processes starting from kanamycin B via intermediate derivatives of kanamycin B in which all the five amino groups are protected with an unsubstituted or substituted benzyloxycarbonyl group and possibly the 2"-hydroxyl group may be protected with a lower alkylsufonyl, arylsulfonyl or aralkylsulfonyl group.

4 Claims, No Drawings

PROCESSES FOR THE PRODUCTION OF 3',4'-DIDEOXYKANAMYCIN B

BACKGROUND OF THE INVENTION

This invention relates to new processes for the production of 3',4'-dideoxykanamycin B.

DESCRIPTION OF THE PRIOR ART

3',4'-Dideoxykanamycin B is a semisynthetic antibiotic having a high antibacterial activity against drug-resistant bacteria and is widely used in clinical applications (see British Pat. No. 1,349,302; U.S. Pat. No. Re. 28,647; "Journal of Antibiotics" Vol. 24, p. 485(1971) and Japanese Patent Publication No. 7595/75).

3',4'-Dideoxykanamycin B, which may hereinafter sometimes referred to as DKB, has the following structural formula:

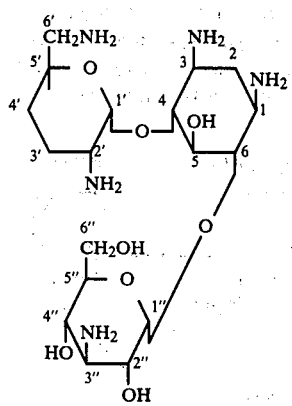

Known method of producing 3',4'-dideoxykanamycin B includes the following two procedures:

(1) Using kanamycin B as the starting material, this is reacted with an alkoxycarbonyl halide to protect the five amino groups of the kanamycin B molecule with the alkoxycarbonyl group as the amino-protecting group, and then a pair of the 3'- and 4'-hydroxyl groups as well as a pair of the 4"- and 6"-hydroxyl groups are protected by reacting with an alkylidenating, arylidenating, cyclohexylidenating or tetrahydropyranylidenating agent to convert them into the form of an acetal or ketal group. The 2"-hydroxyl group is subsequently protected with an alkanoyl or aroyl group known as the conventional hydroxyl-protecting group, and thereafter the protecting group for the pair of the 3'- and 4'-hydroxyl groups is selectively removed by treatment with a dilute acid. In the subsequent steps, the sulfonylation of the 3'- and 4'-hydroxyl groups so liberated, the formation of a double bond between the 3'- and 4'-carbon atoms by treatment of the 3',4'-di-sulfonylated product with an alkali metal bromide or iodide and zinc powder and the hydrogenation of the double bond are successively performed. Thereafter, the protecting group for the pair of the 4"- and 6"-hydroxyl groups is removed by treatment with an acid and finally the remaining amino-protecting groups are removed to produce DKB (see the above-mentioned British Pat. No. 1,349,302; U.S. Pat. No. Re. 28,647 and Japanese Patent Publication No. 7595/75).

(2) The amino groups of kanamycin B used as the starting material are protected by conversion into a group of Schiff-base type, and the a pair of the 3'- and 4'-hydroxyl groups as well as a pair of the 4"- and 6"-hydroxyl groups are protected by the conversion into the form of an acetal or ketal group. The protected kanamycin B derivative so prepared is then subjected to the successive treatments as just mentioned above to produce DKB (see the above-mentioned British Patent and U.S. Reissue Patent).

These procedures of the above known method involve some intricate steps of protecting the amino and hydroxyl groups of the starting kanamycin B and of removing the protecting groups and have been found to give DKB only in a poor overall yield as low as 10%.

In an attempt to provide an improved process for the synthesis of DKB which is free from the aforesaid drawbacks of the above-mentioned method of the prior art, we, the present inventors, have made some research, and we devised a new route for the synthesis of DKB which is disclosed in the specification of pending Japanese Patent application No. 146903/75 filed on Dec. 11, 1975, pending British Patent application No. 49,034/76 filed Nov. 24, 1976 and pending U.S. Patent application Ser. No. 745,015 filed Nov. 26, 1976. For the total synthesis of DKB from kanamycin B, this new route comprises the following consecutive steps of:

reacting kanamycin B with a sulfonic halide of the formula:

wherein $R^a$ represents lower alkyl, aryl or aralkyl group and X represents a halogen atom, in the presence of a base to produce a penta-N-sulfonylated kanamycin B of the formula:

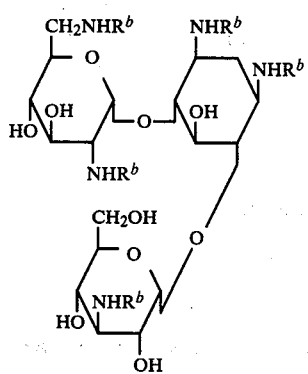

(i)

wherein each $R^b$ represents $-SO_2R^a$ in which $R^a$ is as defined above;

reacting the sulfonylated compound of the formula (i) with an alkylidenating, arylidenating, cyclohexylidenating or tetrahydropyranylidenating agent for protecting a pair of the 4"- and 6"-hydroxyl group to produce a compound of the formula:

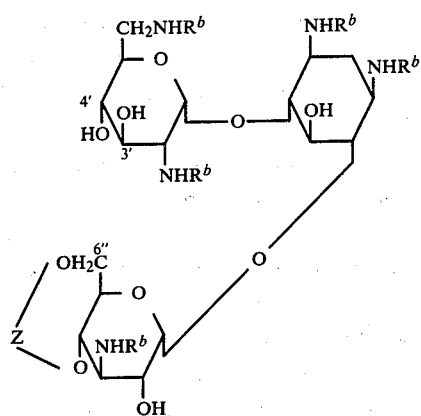

wherein $R^b$ is as defined above and Z represents alkylidene, arylidene, cyclohexylidene or tetrahydropyranylidene group;

further reacting the compound of the formula (ii) with a sulfonic halide of the formula: $R^aSO_2X$ wherein $R^a$ and X are as defined above provided that this sulfonic halide may be the same as or different from that used for the first step of sulfonylation, to produce a compound of the formula:

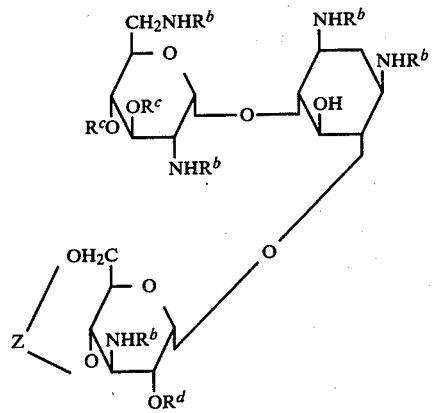

wherein $R^b$ and Z are as defined above, $R^c$ has the same meaning as $R^b$ but may be the same as or different from $R^b$, and $R^d$ represents hydrogen atom or the group $R^c$;

treating the compound of the formula (iii) with a metal iodide to remove the 3'- and 4'-disulfonic ester groups and thereby to produce 3',4'-unsaturated compound of the formula:

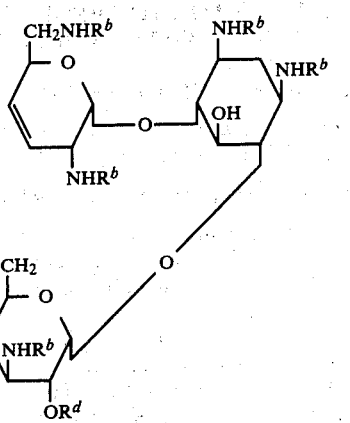

wherein $R^b$, Z and $R^d$ are as defined above;

subjecting the 3',4'-unsaturated compound of the formula (iv) to hydrolysis under weak acidic condition to remove the protecting group-Z- and thereby to produce a compound of the formula:

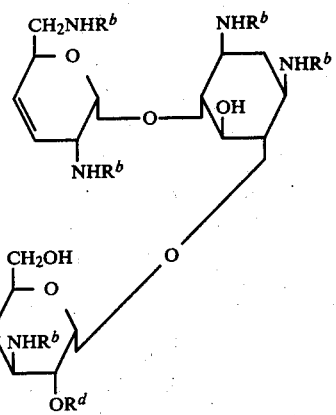

wherein $R^b$ and $R^d$ are as defined above;

treating the compound of the formula (v) with an alkali metal or alkaline earth metal in the presence of liquid ammonia or a lower alkylamine or a mixture of them to remove therefrom the protecting groups $R^b$ and $R^d$, thereby producing 3',4'-dideoxy-3'-eno-kanamycin B of the formula (vi):

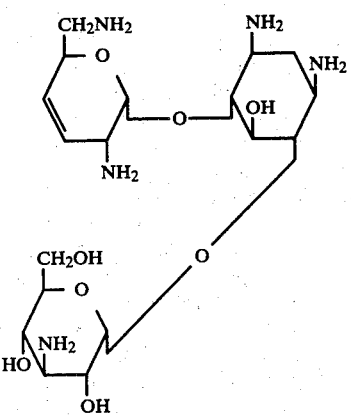

and subjecting the compound (vi) to hydrogenation to produce the final product, 3',4'-dideoxykanamycin B.

The above-mentioned new route for the synthesis of DKB was devised by us on the basis of our new findings that the five amino groups of kanamycin B can also be protected using as the amino-protecting group a sulfonyl group ($R^aSO_2$—) selected from a lower alkylsulfonyl group, arylsulfonyl group and aralkylsulfonyl group which are different in their nature from the alkoxycarbonyl group employed for the same purpose in the known method of the prior art hereinbefore stated; that when the amino-protected kanamycin B derivative of the formula (i) so prepared may then be reacted with an alkylidenating, arylidenating, cyclohexylidenating or tetrahydropyranydenating agent to protect some of the hydroxyl groups of kanamycin B, the pair of the 4''- and 6''-hydroxyl groups can selectively be protected by the conversion of them into the form of an acetal or ketal group without blocking the pair of the 3'- and 4'-hydroxyl groups if the protecting reaction is carried out under certain controlled reaction conditions; that the 4'',6''-O-protected derivative of the formula (ii) so obtained can be converted into a 3',4'-di-O-sulfonylated product or a 3',4',2''-tri-O-sulfonylated product of the formula (iii) by reacting with an appropriate sulfonylating agent; that when this sulfonylated product is treated with an alkali metal iodide, the removal of the 3'- and 4'-sulfonic ester groups takes place to give the corresponding 3',4'-dideoxy-3'-eno derivative of the formula (iv);

that when this 3',4'-dideoxy-3'-eno derivative is treated with a weak acid such as aqueous acetic acid, the protecting group for the pair of the 4''- and 6''-hydroxyl groups may be hydrolytically removed without affecting on the amino-protecting sulfonyl groups and without affecting on the 2''-sulfonic ester group if the latter is present; that the resulting 3',4'-dideoxy-3'-eno derivative of the formula (v) which has been deprotected at the 4''- and 6''-hydroxyl groups is reacted with an alkali metal or an alkaline earth metal in the presence of liquid ammonia, the amino-protecting sulfonyl groups ($R^b$) can be removed; that upon the removal of the amino-protecting groups, the 2''-sulfonyl group can concurrently be removed from the 2''-hydroxyl group if such 2''-sulfonyl group is present as the hydroxyl-protecting group; and that the resulting deprotected derivative (ie. 3'-eno-kanamycin B) of the formula (vi) can be reduced catalytically with hydrogen to give the final product, DKB.

SUMMARY OF THE INVENTION

An object of this invention is to provide a new process for the synthetic production of DKB which is free from the aforesaid drawbacks of the known method of the prior art described in British Pat. No. 1,349,302. The other object is to provide a new improved process for the synthetic production of DKB which is operable with a reduced number of the reaction steps and able to give DKB in a further improved overall yield as compared to the new route for the synthesis of DKB hereinbefore mentioned and disclosed in the specification of co-pending British Patent Application No. 49034/76 for co-pending U.S. Patent application Ser. No. 745,015. Another object will be clear from the following descriptions.

As a result of our further research, we have now found that even when the new route for the synthesis of DKB disclosed in the above-mentioned co-pending British or U.S. patent application is modified by replacing the amino-protecting sulfonyl group by another amino-protecting group which is an unsubstituted or substituted benzyloxycarbonyl group, DKB can be synthetized by the same consecutive steps as above, except that the intermediate 3',4'-di-O-sulfonylated or 3',4',2''-tri-O-sulfonylated kanamycin B derivative needs to be treated with both of an alkali metal iodide and a reducing metal such as zinc powder in order to be converted into the corresponding 3',4'-dideoxy-3'-eno-kanamycin B derivative, and that surprisingly, the overall yield of DKB as calculated on the starting kanamycin B can be improved by approximately 10% or more by effecting such modified process, so that the overall yield of DKB can reach 50% or more.

DETAILED DESCRIPTION OF THE INVENTION

According to a first aspect of this invention, there is provided a process for the production of 3',4'-dideoxykanamycin B of the formula (I):

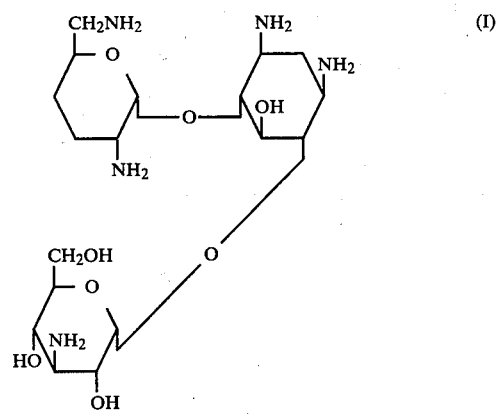

which comprises the steps of:
(a) reacting a compound of the formula (II):

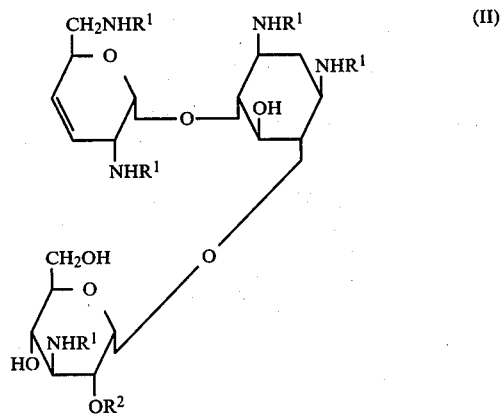

wherein each $R^1$ is an unsubstituted or substituted benzyloxycarbonyl group as the amino-protecting group, and $R^2$ is either hydrogen atom or a lower alkylsulfonyl group, an arylsulfonyl group or an aralkylsulfonyl group as the hydroxyl-protecting group, with an alkali metal or alkaline earth metal in the presence of liquid ammonia to remove the protecting groups $R^1$ and $R^2$ (when $R^2$ is not hydrogen) at once from the compound of the formula (II) and thereby to produce 3',4'-dideoxy-3'-eno-kanamycin B of the formula (III):

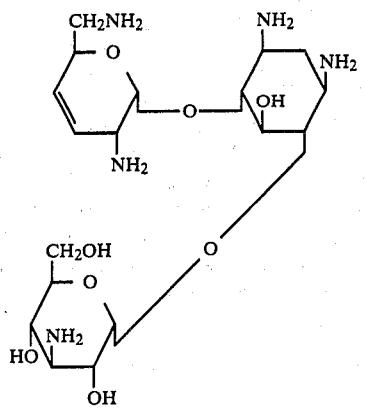 (III)

and (b) reacting the compound of the formula (III) with hydrogen in the presence of a hydrogenation catalyst to hydrogenate the 3',4'-unsaturated bond and to produce 3',4'-dideoxykanamycin B.

The preparation of the protected 3',4'-dideoxy-3'-eno-kanamycin B derivative of the formula (II) which is used as the starting compound for the first aspect process of this invention will be described hereinafter. The amino-protecting group $R^1$ present in the protected 3',4'-dideoxy-3'-eno-kanamycin B derivative (II) is an unsubstituted or substituted benzyloxycarbonyl group of the formula:

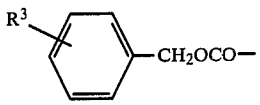

wherein $R^3$ is a hydrogen atom or amino group, a halo group, a lower alkyl group of 1–4 carbon atoms, an aryl group such as phenyl or phenoxy, an aralkyl group such as benzyl, or a benzene ring which is condensed with the phenyl group shown in the above formula to form a naphthalene ring. Suitable examples of the unsubstituted or substituted benzyloxycarbonyl group for the amino-protecting group $R^1$ include benzyloxycarbonyl, p-chlorobenzyloxycarbonyl, p-aminobenzyloxycarbonyl, m- or p-isopropylbenzyloxycarbonyl, p-phenylbenzyloxycarbonyl, p-phenoxybenzyloxycarbonyl and α- or β-naphthylmethyloxycarbonyl groups. The hydroxyl-protecting group $R^2$ is a lower alkylsulfonyl group of 1–4 carbon atoms such as methylsulfonyl, ethylsulfonyl, propylsulfonyl, isopropylsulfonyl and butylsulfonyl; an arylsulfonyl group such as benzenesulfonyl and a substituted benzenesulfonyl, for example, p-toluenesulfonyl, o-nitrobenzenesulfonyl, p-nitrobenzenesulfonyl, p-methoxybenzenesulfonyl and 1- and 2-naphthalenesulfonyl; or an aralkylsulfonyl group such as benzylsulfonyl.

In the step (a) of the first aspect process of this invention, the protected 3',4'-dideoxy-3'-eno-kanamycin B derivative (II) is reacted with an alkali metal or alkaline earth metal in the presence of liquid ammonia. Through this reaction, the amino-protecting group $R^1$ and the hydroxyl-protecting group $R^2$ (if present) are concurrently removed from the compound (II). This reaction may conveniently be conducted in such a manner that the compound (II) is dissolved in liquid ammonia and pieces of one or more of an alkali metal such as lithium, sodium and potassium or an alkaline earth metal such as calcium, magnesium and barium are added to the solution of the compound (II) in liquid ammonia. The reaction temperature may be in a range of −80° C. to −30° C. when liquid ammonia is used. The reaction time may suitably be in a range of 0.2 to 12 hours. The amount of the alkali metal or alkaline earth metal added may suitably be in a range of about 10 to 100 mol per mol of the compound (II). The pieces of the alkali or alkaline earth metal may be added at once but also may be added in portions.

After the reaction is complete, water, a lower alkanol such as methanol or ethanol or ammonium chloride is admixed with the reaction mixture to exhaust the excessive (unreacted) amount of the alkali metal or alkaline earth metal added, the solvent is then removed by evaporation or distillation from the reaction mixture and the residue so obtained is taken up in a volume of water. The resulting aqueous solution is then purified, for example, by a column chromatography on a cation-exchange resin such as Dowex 50W×2 (H cycle) (a product of Dow Chemical Co., U.S.A.) to give a purified product of 3',4'-dideoxy-3'-eno-kanamycin B of the above formula (III).

The 3',4'-dideoxy-3'-eno-kanamycin B so formed is then hydrogenated in the step (b) of the first aspect process of this invention to produce 3',4'-dideoxykanamycin B as the final product. This hydrogenation may be carried out in such a manner that gaseous hydrogen is reacted with a solution of the compound (III) in an inert solvent which is suitably water, an alkanol of 1–4 carbon atoms such as methanol, ethanol and isopropanol or acetone, dioxane, pyridine, tetrahydrofuran, dimethylformamide, cyclohexane and ethyl acetate or a mixture of two or more of them. The presence of a known hydrogenation catalyst such as Raney nickel, platinum, platinum oxide, palladium-on-carbon, palladium oxide, cobalt, rhodium complex, copper and iron is provided in the reaction mixture. The hydrogenation may be effected at a temperature of −40° C. to +120° C. and preferably at ambient temperature or at a temperature of up to 100° C. Although the hydrogenation may readily proceed under atomospheric pressure, it may be effected efficiently under an elevated pressure of eg. 5 to 100 Kg/cm². The reaction time is suitably 0.5 to 48 hours. Owing to this hydrogenation, the double bond between the 3'- and 4'-carbon atoms of the 3',4'-dideoxy-3'-eno-kanamycin B (III) is saturated to produce DKB of the formula (I).

DKB obtained in this way may be purified in a known manner, for example, by a column chromatography, if desired, and it may be converted into its acid-addition salt such as sulfate, hydrochloride, methanesulfonate and the like by reacting with an acid such as sulfuric acid, hydrochloric acid, methanesulfonic acid and the like. When a column chromatographic purification of DKB is made, it is frequent that the purified product of DKB is recovered in the form of the carbonate, as carbon dioxide is absorbed from the atmosphere during the chromatographic operations.

The preparation of the protected 3',4'-dideoxy-3'-eno-kanamycin B derivative of the formula (II) which is employed as a starting material in the first aspect process of this invention may be achieved by the following steps; Thus, kanamycin B (the free base) is reacted with a benzyloxycarbonyl halide reagent of the formula (IV):

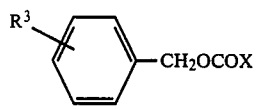

(IV)

wherein $R^3$ is a hydrogen atom, amino group, a halo group, a lower alkyl group, an aryl group or an aralkyl group as stated hereinbefore and X is chlorine or bromine atom, in a manner known per se for the protection of amino group so that the five amino groups of kanamycin B are masked with the amino-protecting group which is the unsubstituted or substituted benzyloxycarbonyl group of the formula:

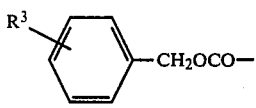

to give a penta-N-benzyloxycarbonylated kanamycin B of the formula (V):

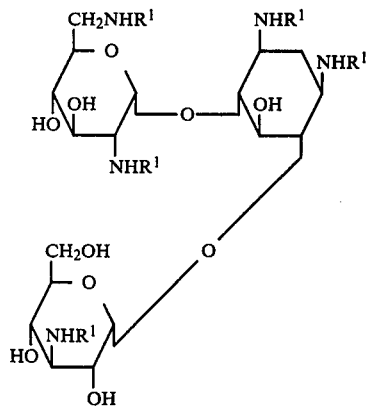

(V)

wherein each $R^1$ has the same meaning as $R^1$ given in the aforesaid formula (II) and is the benzyloxycarbonyl group of the formula

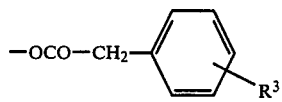

in which $R^3$ is as defined above. The reaction of kanamycin B with the benzyloxycarbonyl-introducing reagent of the formula (IV) may be carried out by interacting kanamycin B and the reagent (IV) substantially in a molar retio of 1:5 in solution in water, a lower alkanol of 1-4 carbon atoms such as ethanol or dioxane or a mixed solvent thereof at a temperature of −30° C. to +50° C. in the presence of an alkali metal hydroxide or an alkali metal carbonate such as sodium carbonate.

The penta-N-benzyloxycarbonylated kanamycin B (V) so prepared is then reacted with an alkylidenating agent, arylidenating agent, cyclohexylidenating agent or tetrahydropyranylidenating agent to convert a pair of the 4''- and 6''-hydroxyl groups into an acetal or ketal group for the purpose of protecting these hydroxyl groups and thereby to give a 4'',6''-O-protected derivative of the formula (VI):

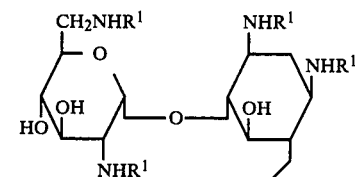

(VI)

wherein $R^1$ is as defined above and Z represents alkylidene, arylidene, cyclohexylidene or tetrahydropyranylidene group: The reaction of the compound (V) with the alkylidenating, arylidenating, cyclohexylidenating or tetrahydropyranylidenating agent is carried out in a suitable aprotic organic solvent such as dimethylformamide in the presence of catalytic amount of an acid such as sulfuric acid and p-toluenesulfonic acid under anhydrous conditions at a lower temperature of eg. 10°-80° C. in such a manner as described in the specification of U.S. Pat. No. 3,929,762. Suitable alkylidenating, arylidenating, cyclohexylidenating or tetrahydropyranylidenating agent for this purpose includes 2,2'-dimethoxypropane, anisaldehyde, 1,1-dimethoxycyclohexane and 1,1-dimethoxytetrahydropyrane. If desired, it is possible to reverse the sequence of the two steps just mentioned above, so that kanamycin B is first reacted with the alkylidenating, arylidenating, cyclohexylidenating or tetrahydropyranylidenating agent for the protection of the 4''- and 6''-hydroxyl groups, followed by the reaction with the reagent (IV) for the protection of the amino groups.

The 4'',6''-O-protected derivative (VI) obtained in the above way is then reacted with a sulfonic halide of the formula (VII):

$$R^4SO_2X \qquad (VII)$$

wherein $R^4$ is a lower alkyl group of 1-4 carbon atoms, an aryl group such as phenyl and naphthyl or an aralkyl group such as benzyl and X is chlorine or bromine atom, to sulfonylate the 3'- and 4'-hydroxyl groups and occasionally the 2''-hydroxyl group and thereby to produce a 3',4'-di-O-sulfonyl or 3',4',2''-tri-O-sulfonyl product of the formula (VIII):

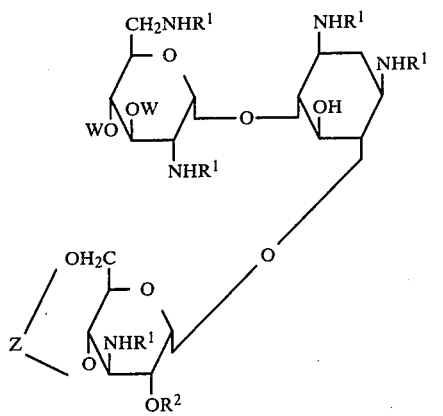

wherein $R^1$ and Z are as defined above, W is sulfonyl group $-SO_2R^4$ in which $R^4$ is as defined above, and $R^2$ is a hydrogen atom or is the same as W, or a mixture of the 3',4'-di-O-sulfonyl product and the 3',4',2''-tri-O-sulfonyl product. The step of producing the sulfonylated product (VIII) may be conducted in a basic solvent such as pyridine or picolin at a low temperature of eg., −30° C. to 50° C.

The sulfonyl product (VIII) is then reacted with an alkali metal iodide or bromide and a reducing metal such as zinc powder to remove the sulfonic ester groups from the 3'- and 4'-positions and thereby to produce the 3',4'-unsaturated derivative (3'-eno derivative) of the formula (IX):

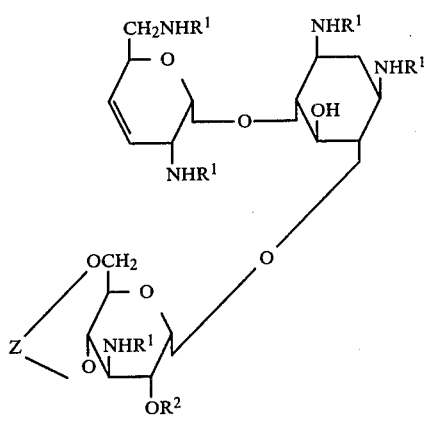

wherein $R^1$, Z and $R^2$ are as defined above. This reaction step may be carried out by admixing an alkali metal iodide such as potassium iodide or sodium iodide as well as a reducing metal such as zinc powder to a solution of the sulfonyl product (VIII) in an inert organic solvent such as dimethylformamide and effecting the reaction at a temperature of 50° to 150° C. for a time of about 15 minutes to 3 hours. When the amino-protecting group for the amino groups of kanamycin B is the benzyloxycarbonyl group as the case be in the present process, we have now found that the combined use of an alkali metal iodide or bromide and a reducing metal such as zinc powder is necessary in order to 3',4'-unsaturate the sulfonylated product (VIII) into the corresponding 3',4'-dideoxy-3'-eno derivative (IX), as be different from the case when the amino-protecting group is a sulfonyl group in accordance with the process of the co-pending Japanese Patent application No. 146903/75, co-pending British Patent application No. 49034/76 and U.S. Patent application Ser. No. 745,015.

The 3',4'-unsaturated derivative (IX) is then treated in a manner known per se in order to remove the alkylidene, arylidene, cyclohexylidene or tetrahydropyranylidene group —Z— which is protecting the 4''- and 6''-hydroxyl groups. The manner for treatment for this purpose depends on the nature of the protecting group —Z—, and the removal of isopropylidene, benzylidene, cyclohexylidene and tetrahydropyranylidene group as the protective group —Z— may be accomplished by mild hydrolysis using diluted hydrochloric acid or aqueous acetic acid. The removal of the 4'',6''-O-protecting group —Z— from the 3'-eno product (IX) gives the amino-protected 3',4'-dideoxy-3'-eno-kanamycin B derivative of the aforesaid formula (II).

For the total synthesis of DKB starting from kanamycin B, therefore, the second aspect of this invention provides a process for the production of DKB, which comprises the consecutive steps of:

(a) reacting kanamycin B with a benzyloxycarbonyl halide of the above formula (IV) to protect the five amino groups of kanamycin B with an unsubstituted or substituted benzyloxycarbonyl group and thereby produce the penta-N-benzyloxycarbonylated kanamycin B of the above formula (V), (b) reacting the compound of the formula (V) with an alkylidenating agent, arylidenating agent, cyclohexylidenating agent or tetrahydropyranylidenating agent to protect a pair of the 4''- and 6''-hydroxyl groups of kanamycin B molecule and thereby produce the 4'',6''-O-protected derivative of the above formula (VI), (c) reacting the compound of the formula (VI) with a sulfonic halide of the above formula (VII) to sulfonylate the 3'- and 4'-hydroxyl groups and occasionally also the 2''-hydroxyl group and thereby produce the 3',4'-di-O-sulfonyl or 3',4',2''-tri-O-sulfonyl product of the above formula (VIII) or a mixture of the 3',4'-di-O-sulfonyl product and the 3',4',2''-tri-O-sulfonyl product, (d) reacting the sulfonyl product of the formula (VIII), either alone or in mixture, with an alkali metal bromide or iodide and a reducing metal to remove 3'- and 4'-sulfonic ester groups from the compound (VIII) and thereby produce the 3',4'-unsaturated derivative of the above formula (IX), (e) treating the compound of the formula (IX) in a manner known per se to remove the group (Z) of protecting the 4''- and 6''-hydroxyl groups and thereby produce the amino-protected 3',4'-dideoxy-3'-eno-kanamycin B dirivative of the aforesaid formula (II), (f) reacting the compound of the formula (II) with an alkali metal or alkaline earth metal in the presence of liquid ammonia to remove the protecting groups $R^1$ and $R^2$ (when the latter is not hydrogen) at once from the compound of the formula (II) and to produce 3',4'-dideoxy-3'-eno-kanamycin B of the aforesaid formula (III), and (g) reacting the compound of the formula (III) with hydrogen in the presence of a hydrogenation catalyst to produce 3',4'-dideoxykanamycin B as the final product.

Furthermore, we have found that the amino-protected 3',4'-dideoxy-3'-eno-kanamycin B derivative of the formula (II) may directly be hydrogenated catalytically with hydrogen to produce the amino-protected 3',4'-dideoxykanamycin B derivative of the formula (X):

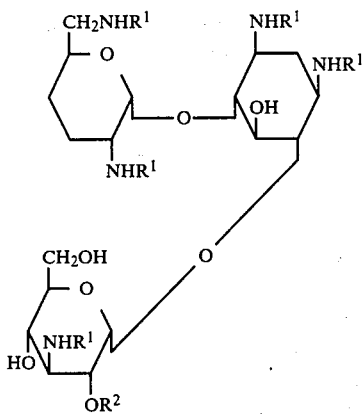

(X)

wherein R¹ and R² are as defined above, and possibly a partially deprotected product thereof which is formed by the removal of a part of the amino-protecting groups (R¹) due to the hydrogenation and that the compound of the formula (X) so obtained and the above-mentioned partially deprotected product may be treated with an alkali metal or alkaline earth metal in the presence of liquid ammonia to remove therefrom the protecting groups R¹ and R² (when the latter is not hydrogen) at once and to produce the desired product, 3',4'-dideoxykanamycin B, too.

According to the third aspect of this invention, therefore, there is provided as a modification of the first aspect process of this invention a process for the production of DKB, which comprises the steps of:

(a) reacting the compound of the above formula (II) with hydrogen in the presence of a hydrogenation catalyst to produce the amino-protected 3',4'-dideoxykanamycin B derivative of the above formula (X), and (b) reacting the compound of the formula (X) with an alkali metal or alkaline earth metal in the presence of liquid ammonia to remove the remaining amino-protecting groups (R¹) and the hydroxyl-protecting group (R² when this is not hydrogen) at once and thereby produce DKB.

The steps (a) and (b) of the third aspect process of this invention may be conducted under the same reaction conditions and in the same manner as in the steps (b) and (a) of the first aspect process of this invention, respectively.

According to the fourth aspect of this invention, there is further provided, as a modification of the second aspect process of this invention, a process for the production of DKB starting from kanamycin B, which comprises the steps (a), (b), (c), (d), and (e) of the second aspect process of this invention, followed by the steps (a) and (b) of the third aspect process of this invention.

In the step (a) of the third aspect process of this invention, the catalytic hydrogenation of the compound (II) gives the amino-protected 3',4'-dideoxy-3'-eno-kanamycin B derivative (X). Upon this hydrogenation, however, a part of the amino-protecting benzyloxycarbonyl groups (R¹) may sometime be removed from the compound (X) depending on the nature of the hydrogenation catalyst employed. Accordingly, it is preferred to employ platinum oxide or palladium oxide as the catalyst, as these catalytic materials are active to selectively hydrogenate the 3',4'-unsaturated bond of the compound (X) without causing the cleavage of the benzyloxycarbonyl groups (R¹). While, the product of the partial deprotection of the compound (X) may be treated as such in the subsequent step (b) of removing the protecting groups to give the desired product DKB.

When the processes according to the first to fourth aspects of this invention are utilized, DKB can be produced from kanamycin B in a favorably high yield and with the following advantages:

(1) The respective steps of synthetizing DKB from kanamycin B are simple to operate, and the overall yield of DKB is 50% or more as calculated on kanamycin B.

(2) The number of the steps involved in the synthesis of DKB is decreased, as a separate step of protecting the 2"-hydroxyl group with an acyl such as alkanoyl and aroyl which was necessary in the known method of the prior art can be omitted, and (3) The removal of the protecting groups from the five amino groups and the 2"-hydroxyl group can be accomplished at once, whereupon no side-reaction takes place.

It is suggested that some of the unsubstituted or substituted benzyloxycarbonyl group which are employed as the amino-protecting group (R¹) in the processes of this invention is generally available for the protection of the amino groups of kanamycin B in the synthesis of a kanamycin B derivative (see Japanese Patent Publication No. 7595/75, British Pat. No. 1,349,302 and U.S. Pat. No. 3,929,762), and it is then exclusively stated that the removal of the benzyloxycarbonyl group from the amino groups is effected by catalytic hydrogenoylis or acid hydrolysis eg. in aqueous acetic acid or hydrobromic acid. In contrast, in order to effect the removal of the benzyloxycarbonyl group from the amino groups, the particular procedure of treating with an alkali metal or alkaline earth metal in the presence of liquid ammonia is adopted according to the processes of this invention in stead of the procedure of the catalytic hydrogenolysis or acid hydrolysis which is conventionally used for the same purpose. Upon the removal of the amino-protecting benzyloxycarbonyl groups, advantageously the processes of this invetion involve simultaneous removal of the hydroxyl-protecting group (the lower alkylsulfonyl, arylsulfonyl or aralkylsulfonyl group) from the 2"-hydroxyl group in case such hydroxyl-protecting group is present. On the other hand, it is known that benzyloxycarbonyl group can be cleaved from the benzyloxycarbonylated amino group by treating the latter with sodium metal in liquid ammonia (see, for example, Sifferd & Vigneaud's article in "J. Biol. Chem." Vol. 108, p. 753 (1935)).

Nonetheless, this known procedure of removing the amino-protecting benzyloxycarbonyl group never have been applied to in the synthetic or semisynthetic production of aminoglycosidic antibiotics. Accordingly, it appears unexpectable that the intricate molecular structure of kanamycin B as one of the aminoglycosidic antibiotics cannot be deteriorated by the treatment with an alkali metal or alkaline earth metal in liquid ammonia, and that the treatment with an alkali or alkaline earth metal in liquid ammonia makes it possible to effect the simultaneous removal of the protecting sulfonyl group from the 2"-hydroxyl group of the kanamycin B molecule.

As will be celar from the foregoing, it is newly found by the present inventors that the amino-protected 3',4'-dideoxy-3'-eno-kanamycin B derivative of the aforesaid formula (II) containing the benzyloxycarbonyl groups for the protection of the five amino groups is usable as a starting material or as an intermediate product for the synthetic production of DKB. This new finding of the present inventors is, in fact, obtained only after the present inventors could discover in the invention of the above-mentioned earlier, copending Japanese Patent application No. 146903/75, co-pending British Patent application No. 49034/76 and co-pending U.S. Patent application Ser. No. 745,015 that the pair of the 4"- and 6"-hydroxyl groups of kanamycin B are selectively converted into an acetal or ketal group for the protection of them without masking the pair of the 3'- and 4'-hydroxyl groups, in case the alkylidenating, arylidenating, cyclohexylidenating or tetrahydropyranylidenating agent is reacted under the controlled reaction conditions as described hereinbefore. On the basis of this discovery, the presen inventors get the success to find out further that the unsubstituted or substituted benzyloxycarbonyl group can be employed in place of the lower alkylsulfonyl, arylsulfonyl or aralkylsulfonyl group for the purpose of protecting the amino groups, that even if the 2"-hydroxyl group can be sulfonylated concurrently upon the sulfonylation of the 3'- and 4'-hydroxyl groups, this cannot adversely affect the subsequent reaction steps of the process, and that rather advantageously the sulfonyl group can be cleaved from the sulfonylated 2"-hydroxyl group simultaneously when the amino-protecting benzyloxycarbonyl groups are removed. Furthermore, as the removal of the amino-protecting group and of the hydroxyl-protecting group from the 2"-hydroxyl group take place substantially quantitatively in the process of this invention, there is attained an unexpectable advantage that this invention further increases the overall yield of DKB (based on kanamycin B used) to about 50% or more which is higher by about 10% than the overall yield of DKB of about 40% normally obtained with the process of the above-mentioned earlier co-pending patent application.

PREFERRED EMBODIMENT OF THE INVENTION

This invention is now illustrated but not limited by the following Examples.

EXAMPLE 1

(1) Production of penta-N-benzyloxycarbonyl-4",6"-O-cyclohexylidene-kanamycin B

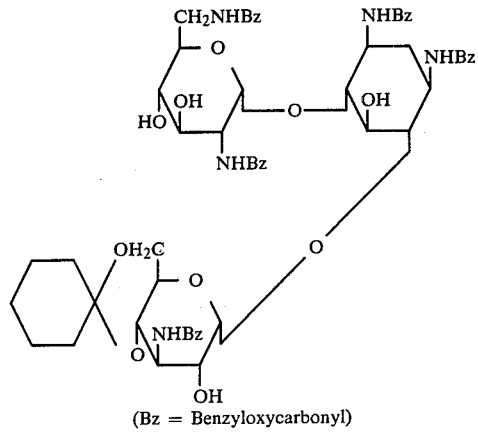

(Bz = Benzyloxycarbonyl)

Kanamycin B (free base) (4.7 g) was dissolved in 50 ml of water, to which was subsequently added 6 g of sodium carbonate and then 100 ml of dioxane, followed by addition of 9.0 g of benzyloxycarbonyl chloride. The admixture so obtained was stirred for 4 hours at ambient temperature. The reaction mixture was concentrated and the concentrated solution was poured into water. The insoluble matter was filtered out, washed with water and then well dried. This solid was taken up into 50 ml of dimethylformamide, to which was then added 4 ml of cyclohexanone dimethylketal (namely, 1,1-dimethoxycyclohexane) and a catalytic amount (100 mg) of anhydrous p-toluenesulfonic acid. The mixture was allowed to stand overnight. The reaction mixture was poured into a large volume of 8 M aqueous ammonia, and the solid so deposited was removed by filtration, washed with water and dried to obtain the title product. Yield 9.68 g (91%). $[\alpha]_D^{20} +48°$ (c 1, pyridine).

Elemental analysis—Calcd. for $C_{64}H_{75}N_5O_{20}$: C, 62.28; H, 6.12; N, 5.67%. Found: C, 62.19; H, 6.18; N, 5.77%.

(2) Production of penta-N-benzyloxycarbonyl-3',4',2"-tri-O-benzylsulfonyl-4",6"-O-cyclohexylidene-kanamycin B

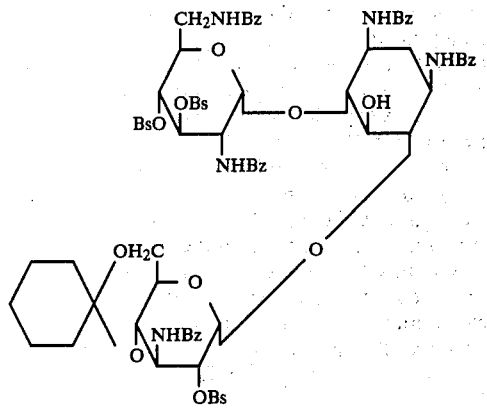

(Bz = Benzyloxycarbonyl, Bs = Benzylsulfonyl)

The product (200 mg) obtained in the above step (1) was dissolved in 4 ml of pyridine, and the resulting solution was cooled to −20° C., to which was then added 123 mg of benzylsulfonyl chloride. The mixture was allowed to stand at that temperature for 4.5 hours and then admixed with 0.1 ml of water in order to decompose the unreacted benzylsulfonyl chloride. The reaction mixture was concentrated by evaporation of the solvent and the concentrated solution was poured into an aqueous solution of 0.05% sodium carbonate. The precipitate deposited was removed by filtration, washed with water and dried to obtain the title product. Yield 272 mg (99%). $[\alpha]_D^{25} +59°$ (c 0.8, dioxane).

Elemental analysis—Calcd. for $C_{85}H_{93}N_5O_{26}S_3$: C, 60.14; H, 5.53; N, 4.13; S, 5.67%. Found: C, 59.90; H, 5.45; N, 4.03; S, 5.67%.

(3) Production of penta-N-benzyloxycarbonyl-2"-O-benzylsulfonyl-4",6"-O-cyclohexylidene-3',4'-dideoxy-3'-eno-kanamycin B

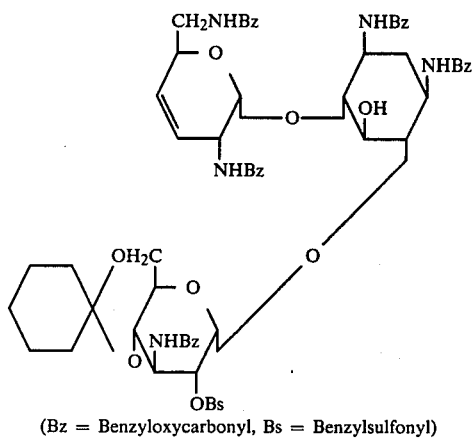

(Bz = Benzyloxycarbonyl, Bs = Benzylsulfonyl)

The product (169 mg) obtained in the above step 2) together with 1.7 g of sodium iodide and 840 mg of zinc powder were suspended in 3.4 mg of dimethylformamide, and the suspension so obtained was stirred at 95° C. for 35 minutes. After cooling, the solidified reaction mixture was extracted with chloroform. The extract in chloroform was washed with water, dried over anhydrous sodium sulfate and concentrated to a syrup. This group was taken up into hot chloroform, and to the resulting solution was added hexane to precipitate a solid substance as the title product. Yield 115 mg (86%). $[\alpha]_D^{25} + 12.5°$ (c 0.8, dioxane). NMR spectrum (in $CDCl_3$); δ 5.6 (2H AB quartet, J=ca. 11 Hz, H-3',4').

Elemental analysis—Calcd. for $C_{71}H_{79}N_5O_{20}S$: C, 62.96; H, 5.88; N, 5.17; S, 2.37%. Found: C, 62.73; H, 5.96; N, 5.04; S, 2.32%.

(4) Production of penta-N-benzyloxycarbonyl-2"-O-benzylsulfonyl-3',4'-dideoxy-3'-eno-kanamycin B

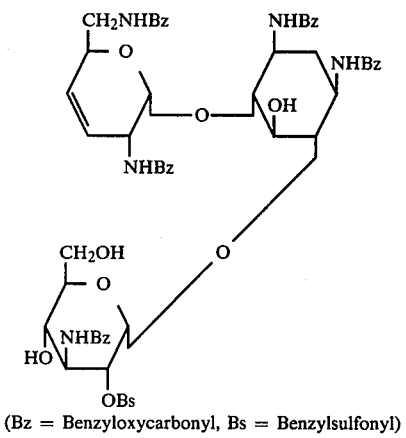

(Bz = Benzyloxycarbonyl, Bs = Benzylsulfonyl)

The product (115 mg) obtained in the above step (3) was dissolved in a mixture of 0.25 ml of dioxane, 0.15 ml of water and 1.6 ml of acetic acid, and the resultant solution was heated for 2.5 hours at 80° C. The reaction solution was concentrated and the solid residue so obtained was taken up into dioxane, to which was then added water to precipitate the title product as a solid. This was collected by filtration and dried. Yield 104 mg (96%). $[\alpha]_D^{25} + 10°$ (c 0.2, dioxane).

Elemental analysis—Calcd. for $C_{65}H_{71}N_5O_{20}S$: C, 61.26; H, 5.62; N, 5.50; S, 2.52%. Found: C, 61.35; H, 5.63; N, 5.22; S, 2.89%.

(5) Production of 3',4'-dideoxy-3'-eno-kanamycin B (according to the first aspect of this invention)

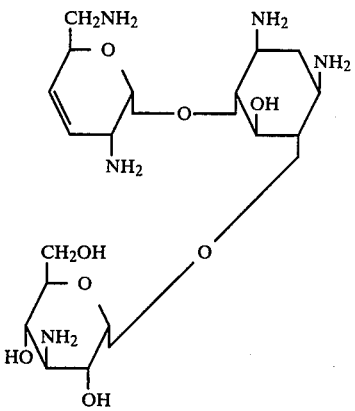

Penta-N-benzyloxycarbonyl-2"-O-benzylsulfonyl-3',4'-dideoxy-3'-eno-kanamycin B (61 mg) obtained in the above step (4) was dissolved in about 18 ml of liquid ammonia at −50° C., followed by addition of about 120 mg of metal sodium. The mixture was gently stirred at −50° C. for 1 hour, followed by addition of methanol to consume up the excess of the metal sodium. The reaction mixture was allowed to slowly raise up to ambient temperature while permitting the ammonia to evaporate. The residue so obtained was dissolved in water, and the aqueous solution was admixed with 4 ml of a cation-exchange resin, Dowex 50W×2 (H cycle) (a product of Dow Chemical Co., U.S.A.) under stirring. The admixture comprising said resin was placed on the top of a column of 3.5 ml of the same resin, Dowex 50W×2, and the whole resin column was well washed with water and then eluted using 1 M aqueous ammonia as the developing solvent. The eluate was collected in fractions, and such fractions which gave positive reaction with ninhydrin were combined together and concentrated to dryness, affording 3',4'-dideoxy-3'-eno-kanamycin B in the form of its mono-carbonate. Yield 23.8 mg (97%). $[\alpha]_D^{25} + 44°$ (c 0.4, water). This compound showed antibacterial activity.

Elemental analysis—Calcd. for $C_{18}H_{35}N_5O_8 \cdot H_2CO_3$: C, 44.61; H, 7.29; N, 13.41%. Found: C, 44.76; H, 7.51; N, 13.75%.

(6) Production of 3',4'-dideoxykanamycin B

The product (12.1 mg) obtained in the above step (5) was dissolved in 0.3 ml of water, to which was then added a catalytic quantity (about 5 mg) of platinium oxide. Hydrogenation was made with hydrogen gas at a pressure of 3.5 kg/cm² for 1.5 hours. The reaction solution was filtered to remove the catalyst, and the filtrate was concentrated to dryness, giving the desired product 3',4'-dideoxykanamycin B in the form of its monocarbonate. Yield 11.5 mg (95%). $[\alpha]_D^{25} + 110°$ (c 1, water). The overall yield of 3',4'-dideoxykanamycin B based on the starting kanamycin B was 57%. The product obtained in this Example was fully coincident with an authentic sample of DKB previously prepared, with respect to their NMR spectrum, IR spectrum and antibacterial spectrum.

Elemental analysis—Calcd. for $C_{18}H_{37}N_5O_8 \cdot H_2CO_3$: C, 44.43; H, 7.66; N, 13.64%. Found: C, 44.91; H, 7.96; N, 13.63%.

EXAMPLE 2

(1) Production of penta-N-benzyloxycarbonyl-2''-O-benzylsulfonyl-3',4'-dideoxykanamycin B (according to the third aspect of this invention)

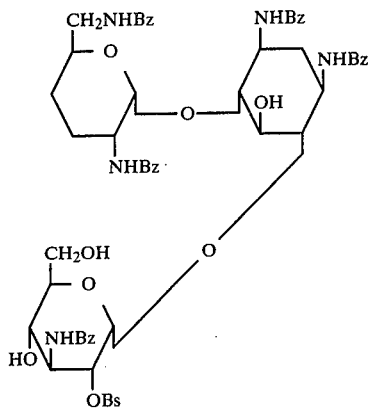

(Bz = Benzyloxycarbonyl, Bs = Benzylsulfonyl)

Penta-N-benzyloxycarbonyl-2''-O-benzylsulfonyl-3',4'-dideoxy-3'-eno-kanamycin B (108 mg) obtained as the product of the step (4) of Example 1 was dissolved in 3.0 ml of a mixture of water and dioxane (1:1 by volume), to which was added 30 mg of platinum oxide. The hydrogenation was made in the same way as in the step (6) of Example 1. The hydrogenation product comprising the title product was obtained in a yield of 106 mg (98%).

(2) Production of 3',4'-dideoxykanamycin B

The hydrogenation product obtained in the above step (1) of this Example was dissolved in liquid ammonia at −50° C. and then treated in the same manner as in the step (5) of Example 1 to remove the protecting groups, that is, the benzyloxycarbonyl groups and the benzylsulfonyl group. 3',4'-dideoxykanamycin B monocarbonate was obtained in a yield of 39 mg (95% based on the penta-N-benzyloxycarbonyl-2''-O-benzylsulfonyl-3',4'-dideoxy-3'-eno-kanamycin B). $[\alpha]_D^{25} +109°$ (c 1, water). The overall yield of DKB in this Example was 51% based on the starting kanamycin B.

What we claim is:

1. A compound of the formula

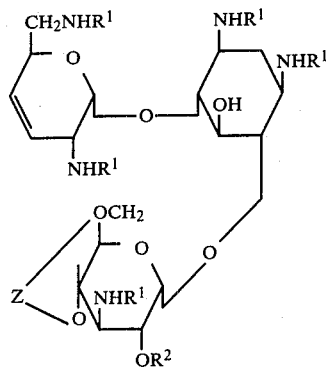

wherein
R[1] is benzyloxycarbonyl, p-chlorobenzyloxycarbonyl, p-aminobenzyloxycarbonyl, m-isopropylbenzyloxycarbonyl, p-isopropylbenzyloxycarbonyl, p-phenylbenzyloxycarbonyl, p-phenoxybenzyloxycarbonyl, α-naphthylmethyloxycarbonyl or β-naphthylmethyloxycarbonyl,
R[2] is lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl, and
Z is lower alkylidene, arylidene formed from benzaldehyde, anisaldehyde or tolualdehyde, cyclohexylidene or tetrahydropyranylidene.

2. Penta-N-benzyloxycarbonyl-2''-O-benzylsulfonyl-4'',6''-O-cyclohexylidene-3',4'-dideoxy-3'-eno-kanamycin B.

3. A compound of the formula

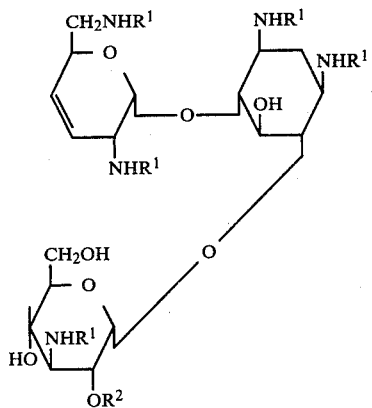

wherein
R[1] is benzyloxycarbonyl, p-chlorobenzyloxycarbonyl, p-aminobenzyloxycarbonyl, m-isopropylbenzyloxycarbonyl, p-isopropylbenzyloxycarbonyl, p-phenylbenzyloxycarbonyl, p-phenoxybenzyloxycarbonyl, α-naphthylmethyloxycarbonyl or β-naphthylmethyloxycarbonyl, and
R[2] is lower alkyl-sulfonyl, arylsulfonyl selected from the group consisting of benzenesulfonyl, p-toluenesulfonyl, o-nitrobenzenesulfonyl, p-nitrobenzenesulfonyl, p-methoxybenzenesulfonyl, 1-naphthalenesulfonyl and 2-naphthalenesulfonyl or benzylsulfonyl.

4. penta-N-Benzyloxycarbonyl-2''-O-benzylsulfonyl-3',4'-dideoxy-3'-eno-kanamycin B.

* * * * *